US00RE34185E

United States Patent [19]

Amick

[11] E Patent Number: Re. 34,185

[45] Reissued Date of Patent: Feb. 23, 1993

[54] STABILIZATION OF NON-AQUEOUS SOLUTIONS OF 3-ISOTHIAZOLONES

[75] Inventor: David R. Amick, Chalfont, Pa.

[73] Assignee: Rohm and Haas Company, Philadelphia, Pa.

[21] Appl. No.: 606,222

[22] Filed: Oct. 31, 1990

Related U.S. Patent Documents

Reissue of:

[64] Patent No.: 4,824,957
Issued: Apr. 25, 1989
Appl. No.: 80,933
Filed: Aug. 3, 1987

U.S. Applications:

[63] Continuation-in-part of Ser. No. 709,755, Mar. 8, 1985, abandoned.

[51] Int. Cl.[5] ..... C07D 275/03; A01N 43/80

[52] U.S. Cl. ..... 548/213

[58] Field of Search ..... 548/213; 514/372

[56] References Cited

U.S. PATENT DOCUMENTS

| | | | |
|---|---|---|---|
| 3,870,795 | 3/1975 | Miller et al. | 548/213 |
| 4,067,878 | 1/1978 | Miller et al. | 548/101 |
| 4,188,376 | 2/1980 | Payne et al. | 514/373 |
| 4,241,214 | 12/1980 | Miller et al. | 548/101 |
| 4,281,136 | 7/1981 | Virgillo et al. | 548/206 |
| 4,396,413 | 8/1983 | Miller et al. | 71/67 |

FOREIGN PATENT DOCUMENTS

| | | | |
|---|---|---|---|
| 0166611 | 1/1986 | European Pat. Off. . | |
| 0194146 | 9/1986 | European Pat. Off. . | |
| 5140726 | 1/1979 | Japan | 548/213 |
| 56-99401 | 8/1981 | Japan | 514/372 |
| 2004747A | 4/1979 | United Kingdom . | |

OTHER PUBLICATIONS

Lachman et al., "The Theory and Practice of Industrial Pharmacy", 2nd ed., Lea & Febiger, Philadelphia, 1976, pp. 32–43.

*Primary Examiner*—Diana G. Rivers
*Attorney, Agent, or Firm*—Michael B. Fein

[57] ABSTRACT

Non-aqueous solutions of 3-isothiazolones are stabilized against chemical decomposition by using organic hydroxylic solvents. These compositions exhibit bactericidal, fungicidal and algaecidal properties.

9 Claims, No Drawings

STABILIZATION OF NON-AQUEOUS SOLUTIONS OF 3-ISOTHIAZOLONES

Matter enclosed in heavy brackets [ ] appears in the original patent but forms no part of this reissue specification; matter printed in italics indicates the additions made by reissue.

This application is a continuation-in-part application of U.S. Ser. No. 709,755, filed Mar. 8, 1985, now abandoned.

This invention relates to solvent stabilized solutions of 3-isothiazolones, their preparation, compositions containing them, and their use in controlling living organisms.

Isothiazolones of the present invention are represented by the following structural formula:

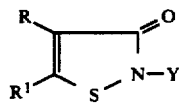

I wherein

Y is an unsubsituted or substituted alkyl of from 1 to 8 carbon atoms, an unsubstituted or halo substituted alkenyl or alkynyl of 2 to 8 carbon atoms, and, preferably, from 2 to 4 carbon atoms, an unsubstituted or substituted cycloalkyl of from 5 to 8 carbon atoms, an unsubstituted or substituted aralkyl or an unsubstituted or substituted aryl;

R hydrogen, halo, or a $(C_1-C_4)$alkyl and $R^1$ is hydrogen, halogen or $(C_1-C_4)$alkyl.

Representative Y substituents include methyl, ethyl, propyl, isopropyl, butyl, hexyl, octyl, cyclohexyl, benzyl, 3,4-dichlorobenzyl, 4-methoxybenzyl, 4-chlorobenzyl, 3,4-dichlorophenyl, 4-methoxyphenyl, hydroxymethyl, chloromethyl, chloropropyl and the like.

In many instances it is desirable to completely or eliminate water, salt, and nitrate levels in isothiazolone biocides. For example, certain emulsions or dispersions require biocidal protection and are sensitive to shock resulting in a precipitate when salts, especially those containing divalent ions, are added. This precipitation precludes the use of biocides containing appreciable salt levels, especially in situations where mechanical stirring is not feasible.

In oils and fuels it is desirable to have a substantially water-free and salt-free environment. Water in contact with the organic matter in fuel creates conditions suitable for biological growth and the formation of sludge. Also, salts in oils and fuel result in ignition deposits which lead to clogging and corrosion of various mechanical components.

In some cosmetic formulations, it is also important to have low water and salt content. Eliminating nitrate salts avoids the possibility of nitrosamine formation. Nitrosamines are suspected carcinogens.

This invention is directed to stable biocidal isothiazolone compositions in which (1) water is substantially eliminated, (2) neutralizing salt content is eliminated and (3) nitrate stabilizer salts are substantially reduced.

The preferred compositions contain from about 3 to about 10% by weight of one or more isothiazolones, no water, 0 to 1% of a stabilizing salt, and a stabilizing amount of hydroxy solvent(s) which may be present in an amount up to about 99.5% of a hydroxy solvent or mixture of said solvents. It is to be understood that water could be added to the compositions of this invention but that the stability would be lower than those containing no water.

The stabilizing hydroxy solvents of this invention are selected from those having the following structural formula:

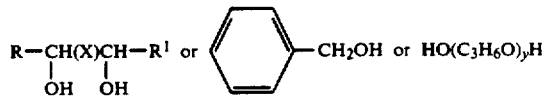

IIa IIb IIc wherein R and $R^1$ are hydrogen or lower alkyl, such as methyl, ethyl, propyl, butyl, pentyl and the like and X is $-(CH_2)_n-$ where n is an integer of 1 to 4 and y is an integer of from 2 to about 150.

[Preferred stabilizing solvents include benzyl alcohol, dipropylene glycol, polypropylene glycol and 1,5-pentanediol.] *The stabilizing hydroxy solvent(s) useful in this invention are selected from the group consisting of dipropylene glycol, polypropylene glycol, 1,5-pentadiol, propylene glycol, ethylene glycol, diethylene glycol, triethylene glycol, and benzyl alcohol.*

The stabilizing solvent is generally employed in an amount of from about 89 to about 99.5% by weight of the composition, with the most preferred amount depending on the amount of isothiazolone desired.

Prior to this discovery it was known to employ organic solvents with metal nitrates (See especially U.S. Pat. No. 3,870,795, Col. 3, lines 39–54). However, the solvents were not known to be useful as stabilizers. U.S. Pat. No. 3,870,795, Col. 4, lines 35–45 discloses that non-aqueous solutions containing about 15% of 5-chloro-2-methyl-3-isothiazolone/2-methyl-3-isothiazolone (93:7) in dipropylene glycol completely decomposed in 28 days at 50° C.

U.S. Pat. Nos. 4,241,214 and 4,396,413 describe metal salt complexes of I, supra and their use as effective biocidal agents. Current commercial products containing products of formula I, supra are sold as aqueous solutions containing divalent nitrate salts which serve as stabilizers for the isothiazolones which would otherwise decompose upon storage.

Japanese Pat. No. 1,318,306 claims stabilizing an isothiazolone (with high amounts (7%) of stabilization salts) and 2-hydroxymethyl-2-nitro-1,3-propanediol with a diol solvent. Also, the water content is identified as being in the range of 15 to 75%. However, 2-hydroxymethyl-2-nitro-1,3-propanediol is a known formaldehyde releaser, which is known to stabilize isothiazolones (Lee U.S. Pat. Nos. 4,165,318 and 4,129,448). This patent then describes the diols used-ethylene glycol, diethylene glycol, polyethylene glycol, propylene glycol, dipropylene glycol or polypropylene glycol. However, our tests show that ethylene glycol, propylene glycol and polyethylene glycol (triethylene glycol) are much less effective in the non-formaldehyde containing compositions.

This invention permits the stabilization of isothiazolones without employing stabilization salts. It should be understood that the use of small amounts of stabilizing salts is also within the scope of this invention. Useful stabilization salts which can be employed are those disclosed in U.S. Pat. Nos. 3,870,795 and 4,067,878. Preferred stabilization salts fall into two groups:

(1) Metal nitrates, where the metal is barium, cadmium, calcium, chromium, cobalt, copper, iron, lead, lithium, magnesium, manganese, mercury, nickel, sodium, silver, strontium, tin, zinc and the like; and (2) Copper (2+) salts where the anion is halide, sulfate, nitrate, nitrite, acetate, chlorate, perchlorate, bisulfate, bicarbonate, oxalate, maleate, carbonate, or phosphate.

Previously in the preparation of the 3-isothiazolones, it was desired to partially neutralize the intermediate isothiazolone hydrochloride salt to obtain a more stable product; this resulted in the formation of a "neutralization salt" as a by-product. This invention eliminates the neutralization salt, as the hydrogen chloride formed in the preparation of the isothiazolones is removed by treating the isothiazolone hydrochloride salt with an organic base. Tertiary organic bases are preferred, for example, trialkylamines such as trimethylamine, triethylamine, tripropylamine and the like, also cyclic tertiary amines such as pyridine and the like. While an inorganic salt can be used to neutralize the hydrogen chloride, it dissolves and reacts very slowly in the "all organic" formulation, and results in the formation of a neutralization salt which is undesirable.

Typical formulation ranges are illustrated in the following Table I (all percentages are parts by weight)

TABLE I

| | Hydroxy Solvent | Stabilization Salt |
|---|---|---|
| Isothiazoline | | |
| 0.5-10 | 89-99.5 | 0-1.0 |
| Preferred | | |
| 3.0-10.0 | 89.0-97.0 | 0-1.0 |
| Most Preferred | | |
| 6.0-10.0 | 89.0-93.7 | 0.3-1.0 |

Solutions of isothiazolones are used as watercooling system microbicides, as preservatives for aqueous dispersions or organic polymers, as wood pulp white water slimicides, as cosmetic preservatives, as cutting oil, jet fuel, and heating oil preservatives, and the like. Solutions of isothiazolones are also applied to a solid substrate, such as fabric, leather, or wood, as a preservative.

The products of this invention are especially useful as preservatives for the following: 1. Cosmetics, as it eliminates or substantially reduces the presence of nitrates which under certain conditions in the presence of amines or amine precursors may lead to the formation of nitrosoamines. 2. Oils and fuels, since added salts and moisture are eliminated or minimized thus preventing potential corrosion, deposition or sludge formation 3. Emulsions and dispersions that are sensitive to the addition of salts. Examples of these emulsions and dispersions are those contained in a wide variety of products, such as paints, cosmetics, floor polishes and binders.

The following examples will further illustrate this invention, but are not intended to limit it in any way. All parts and percentages are by weight and all temperatures in degrees Centrigrade, unless otherwise stated.

Our studies show that the temperature of 55° C. causes an acceleration effect so that one week is equivalent to about 3 months at 25° C.; two weeks is equivalent to about 6 months; three weeks is equivalent to 9 months; and four weeks is equivalent to about 12 months, and so on. The temperature of 65° C. causes an acceleration effect so that one week is equivalent to about 7 months at 25° C.; two weeks is equivalent to 14 months; three weeks is equivalent to 21 months; four weeks is equivalent to 28 months, and so on. Any product which does not show signs of decomposition in one year (4 weeks at 55° C. or about 2 weeks at 65° C.) is considered to be a stable product.

Example 1

Stability (by HPLC) of 5-chloro-2-methyl-4-isothiazolin-3-one in Organic Solvents at 65° C. ("No $H_2O$") (1% AI to start)

| Solvent | 2 days | 2 weeks | 4 weeks | 6 weeks |
|---|---|---|---|---|
| (a) Dipropylene glycol | P | P | P | P |
| (b) Polypropylene glycol (MW = 2000) | P | P | P | P |
| (c) 1,5-Pentanediol | P | P | P | F |
| (d) Propylene glycol | P | P | F | F |
| (e) Ethylene glycol | P | P | F | F |
| (f) Diethylene glycol | P | P | F | F |
| (g) Triethylene glycol | P | P | F | F |
| (h) 2,3-Pentanediol | P | F | F | F |

AI (Active Ingredient determined by HPLC (HPLC = High Pressure Liquid Chromatography)
P = essentially no loss of AI
F = AI totally decomposed Example 2

Stability (by HPLC) of 5-chloro-2-methyl-4-isothiazolin-3-one in Organic Solvents (90%) with 10% Water at 65° C. (1% AI to start)

| Organic Solvent | 1 week | 2 weeks | 3 weeks | 4 weeks |
|---|---|---|---|---|
| (a) Dipropylene glycol | P | P | P | F |
| (b) Benzyl alcohol | P | P | P | P |
| (c) 15-Pentanediol | P | P | P/F | F |
| (d) Propylene glycol | P | F | — | — |
| (e) Ethylene glycol | P | F | — | — |
| (f) Diethylene glycol | P | P/F | F | — |
| (g) Triethylene glycol | P/F | F | — | — |
| (h) 2,4-Pentanediol | P | F | — | — |
| (i) Triethylene glycol, dimethyl ether | F | — | — | — |
| (j) Acetonylacetone | P/F | F | — | — |
| (k) Dimethylsulfoxide | F | — | — | — |

P/F = 20-80% of AI decomposed (by HPLC)

EXAMPLE 3

Hair Shampoo—Nitrate and Nitrite Free

A solution containing 3% active isothiazolines N-methyl-5-chloroisothiazolin-3-one and N-methylisothiazolin-3-one, 2% NaCl, 3% water in dipropylene glycol is used as a preservative for a hair shampoo. The biocide solution will contain no nitrate, nitrite or nitrosamines. The shampoo is treated with biocide solution to provide 20 ppm of active biocide. The resultant shampoo contains no nitrosamine and has no nitrate to react with amines in the shampoo composition.

Example 4

Preparation of a 7.5% Formulation of Active Ingredient (A.I.)

To a 500 ml-rb flask equipped with a mechanical stirrer, thermometer, and dropping funnel were added 41.25 g of powdered N-methyl-5-chloroisothiazolin- 3-one (80%)/N-methyl isothiazolin-3-one (20%) (A.I.) HCl salt and 83.75 g toluene. The mixture was stirred and cooled (≦15° C.) as 15 g of triethylamine was added dropwise over 20 min. Five minutes after the addition was completed the $ET_3N$. HCl salt was removed by filtration to afford a toluene solution of A.I. as the filtrate. A 22.3 gm portion of the toluene solution was mixed with 25 gm of 1% $Cu(NO_3)_n$/dipropylene glycol solution to afford a clear solution having a pH >7; the pH was adjusted to 3.57 by adding several drops of conc. HCl. This solution was rotovapped 1 hr at 55° C./20 mm Hg to remove 8.48 gms of toluene, which was replaced with 8.48 gms of dipropylene glycol to afford about 7.5% A.I., pH 2.71, and a $Cu(NO_3)_2$ level of about 0.5%.

TABLE II

| Heat-Age Stability of 7.5% AI Formulation | | |
|---|---|---|
| | Weeks Aged With No Loss of AI | |
| % AI | 55° C. | 65° C. |
| 7.5 | ≧5 wks | 4–5 wks |

It is to be understood that changes may be made to the examples without departing from the scope of this invention as defined by the claims.

I claim:

[1. A method for stabilizing a 0.5 to about 10% by weight solution of an isothiazolone of the formula:

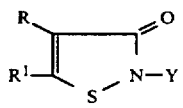

I wherein

Y is an unsubstituted alkyl of 1 to 8 carbon atoms, an unsubstituted or halo substituted alkenyl or alkynyl of 2 to 8 carbon atoms, an unsubstituted cycloalkyl of 5 to 8 carbon atoms, benzyl, aralkyl selected from 3,4-dichlorobenzyl, 4-methoxybenzyl or 4-chlorobenzyl or substituted aryl selected from 3,4-dichlorophenyl or 4-methoxyphenyl; R is halo; $R^1$ is hydrogen, halogen or $(C_1-C_4)$alkyl which consists of formulating a solution of the isothiazolone by dissolving the isothiazolone in from about 90 to about 99% by weight of dipropylene glycol, polypropylene glycol, 1,5-pentadiol or benzyl alcohol.]

[2. The method of claim 1 wherein the isothiazolone is 5-chloro-2-methyl-4-isothiazolin-3-one.]

[3. The method of claim 1 wherein the solvent is dipropylene glycol.]

[4. A stabilized solution consisting essentially of from 0.5 to 10% by weight of a compound of the formula:

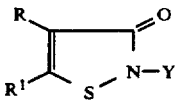

I wherein

Y is an unsubstituted alkyl of 1 to 8 carbon atoms, an unsubstituted or halo substituted alkenyl or alkynyl group of 2 to 8 carbon atoms, an unsubstituted cycloalkyl of 5 to 8 carbon atoms, benzyl, or 3,4-dichloro phenyl or 4-methoxy phenyl R is halo; $R^1$ is hydrogen, halogen or $(C_1-C_4)$ alkyl, and from 90 to 99.5% by weight of dipropylene glycol, polypropylene glycol, 1,5-pentanediol or benzyl alcohol.]

[5. The solution of claim 4 wherein the isothiazolone is 5-chloro-2-methyl-4-isothiazolin-3-one.]

[6. The solution of claim 4 wherein the solvent is dipropylene glycol.]

*7. A method for stabilizing a 0.5 to about 10% by weight solution of an isothiazolone of the formula:*

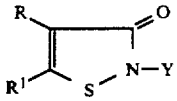

I

*wherein*

*Y is an unsubstituted alkyl of 1 to 8 carbon atoms, an unsubstituted or halo substituted alkenyl or alkynyl of 2 to 8 carbon atoms, an unsubstituted cycloalkyl of 5 to 8 carbon atoms, benzyl, aralkyl selected from 3,4-dichlorobenzyl, 4-methoxybenzyl or 4-chlorobenzyl or substituted aryl selected from 3,4-dichlorophenyl or 4-methoxyphenyl; $R^1$ is halo; R is hydrogen, halogen or $(C_1-C_4)$ alkyl which consists of formulating a solution of the isothiazolone by dissolving the isothiazolone in from about 90 to about 99% by weight of dipropylene glycol, polypropylene glycol, 1,5-pentadiol or benzyl alcohol.*

*8. The method of claim 7 wherein the isothiazolone is 5-chloro-2-methyl-4-isothiazolin-3-one.*

*9. The method of claim 7 wherein the solvent is dipropylene glycol.*

*10. A stabilized solution consisting essentially of from 0.5 to 10% by weight of a compound of the formula:*

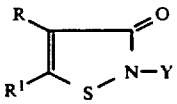

I

*wherein*

*Y is an unsubstituted alkyl of 1 to 8 carbon atoms, an unsubstituted or halo substituted alkenyl or alkynyl group of 2 to 8 carbon atoms, an unsubstituted cycloalkyl of 5 to 8 carbon atoms, benzyl, or 3,4-dichloro phenyl or 4-methoxy phenyl*

*$R^1$ is halo; R is hydrogen, halogen or $(C_1-C_4)$ alkyl, and from 90 to 99.5% by weight of dipropylene glycol, polypropylene glycol, 1,5-pentanediol or benzyl alcohol.*

*11. The solution of claim 10 wherein the isothiazolone is 5-chloro-2-methyl-4-isothiazolin-3-one.*

*12. The solution of claim 10 wherein the solvent is dipropylene glycol.*

*13. A method for stabilizing a 0.5 to about 10% by weight solution of an isothiazolone of the formula:*

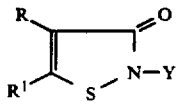

*wherein*

*Y is an unsubstituted alkyl of 1 to 8 carbon atoms, an unsubstituted or halo substituted alkenyl or alkynyl of 2 to 8 carbon atoms, an unsubstituted cycloalkyl of 5*

*to 8 carbon atoms, benzyl, aralkyl selected from 3,4-dichlorobenzyl, 4-methoxybenzyl or 4-chlorobenzyl or substituted aryl selected from 3,4-dichlorophenyl or 4-methoxyphenyl; $R^1$ is halo; R is hydrogen, halogen or ($C_1$–$C_4$) alkyl which consists of formulating a solution of the isothiazolone by dissolving the isothiazolone in from about 90 to about 99% by weight of a solvent selected from the group consisting of ethylene glycol, dipropylene glycol, polypropylene glycol, 1,5-pentanediol, propylene glycol, diethylene glycol, and triethylene glycol, in the absence of water.*

*14. A stabilized solution consisting of essentially from 0.5 to 10% by weight of a compound of the formula:*

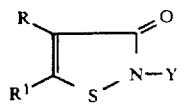

*wherein*

*Y is an unsubstituted alkyl of 1 to 8 carbon atoms, an unsubstituted or halo substituted alkenyl or alkynyl group of 2 to 8 carbon atoms, an unsubstituted cycloalkyl of 5 to 8 carbon atoms, benzyl, or 3,4-dichlorobenzyl, 4-methoxybenzyl; $R^1$ is halo; R is hydrogen, halogen or ($C_1$–$C_4$) alkyl, and from 90 to 99% by weight of a solvent selected from the group consisting of ethylene glycol, dipropylene glycol, polypropylene glycol, 1,5-pentanediol, propylene glycol, diethylene glycol and triethylene glycol, said solution containing no water.*

*15. The solution of claim 14 wherein said compound is 5-chloro-2-methyl-4-isothiazoline-3-one.*

* * * * *